United States Patent
Blau

(10) Patent No.: US 6,765,115 B1
(45) Date of Patent: Jul. 20, 2004

(54) METHOD FOR PREPARING DIMETAL SULFONYL AMIDE SALTS

(75) Inventor: Hanne Anna Katharina Blau, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 134 days.

(21) Appl. No.: 10/129,169

(22) PCT Filed: Nov. 16, 2000

(86) PCT No.: PCT/US00/31597

§ 371 (c)(1),
(2), (4) Date: May 1, 2002

(87) PCT Pub. No.: WO01/38300

PCT Pub. Date: May 31, 2001

Related U.S. Application Data

(60) Provisional application No. 60/167,020, filed on Nov. 23, 1999.

(51) Int. Cl.⁷ ...................... C07L 311/09; C07L 303/40

(52) U.S. Cl. ............................. 564/89; 564/90; 564/96
(58) Field of Search ................. 564/89, 90, 96

(56) References Cited

U.S. PATENT DOCUMENTS

| 5,463,005 A | 10/1995 | Desmarteau |
| 6,252,111 B1 * | 6/2001 | Sakai et al. .................. 564/82 |
| 6,319,428 B1 * | 11/2001 | Michot et al. ............. 252/500 |

OTHER PUBLICATIONS

Von Johann N. Meubdoerffer, et al. Bisperfluoralkansulfonylimide, Chemiker Zeitung, (19872) pp. 582–583, vol. 96.

Behrend, et al. Trifluormethyl–Schwefel–stickstoff–verbindungen, Journal of Fluorine Chemistry, (1974) pp. 99–106, vol. 4.

* cited by examiner

*Primary Examiner*—Peter O'Sullivan

(57) ABSTRACT

Disclosed is a process for producing sulfonyl amide salts useful as imidizing agents in the preparation of sulfonyl imides.

13 Claims, 1 Drawing Sheet

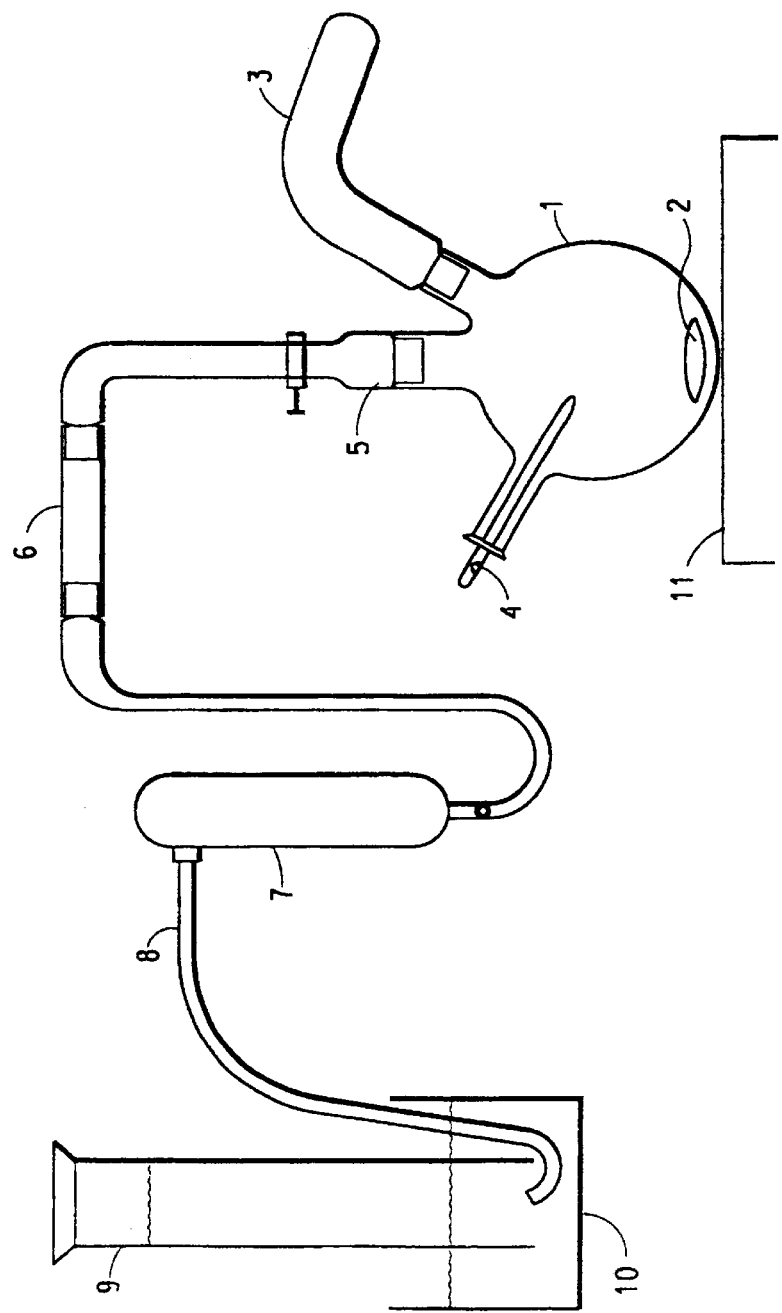

METHOD FOR PREPARING DIMETAL SULFONYL AMIDE SALTS

This application is a 371 of PCT/US00/31597, filed Nov. 16, 2000, which claims the benefit of U.S. provisional application 60/167,020, filed Nov. 23, 1999.

FIELD OF THE INVENTION

The present invention is directed to a high yield process for producing dimetal sulfonyl amide salts which are highly useful as imidizing agents in the preparation of sulfonyl imides, which are in turn useful as strong acid catalysts, as electrolyte salts in electrochemical cells, and as monomers suitable for incorporation into ionomers. The products disclosed are useful in electrochemical applications such as batteries, fuel cells, electrolysis cells, ion exchange membranes, sensors and electrochemical capacitors.

BACKGROUND OF THE INVENTION

Methods for imidizing chemical compositions containing sulfonyl fluorides particularly fluorinated sulfonyl fluorides are known in the art. For example, DesMarteau, U.S. Pat. No. 5,463,005, discloses substituted perfluoro-olefins of the formula

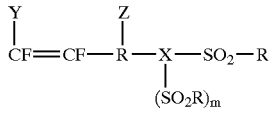

where X=CH or N, Z=H, K, Na, or Group I or II metal, R=one or more fluorocarbon groups including fluorocarbon ethers and/or sulfonyl groups and/or perfluoro non-oxy acid groups, Y=perfluoroalkyl or F, and m=0 or 1.

Xue, Ph.D. thesis, Clemson University, 1996, discloses the formation of the monomer $$CF_2=CF-OCF_2CF_2SO_2N(Na)SO_2CF_3$$

by reaction of $CF_2=CF-OCF_2CF_2SO_2Cl$ with $CF_3SO_2NHNa$ in the presence of $Na_2CO_3$ in acetonitrile Further disclosed by Xue, op.cit,, is $CF_3SO_2NNa_2$ made by reacting a mixture of $CF_3SO_2NHNa$ and NaH in THF for four hours at room temperature. Xue's $CF_3SO_2NNa_2$ composition is reacted with a cyclic sulfone of the formula

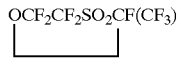

to produce the vinyl ether monomer, $CF_2=CF-OCF_2CF_2SO_2N(Na)SO_2CF_3$ at a yield of 4%, the remainder of the product being two saturated species, both present in larger quantities.

Behrend and Haas, J. Fluorine Chem. 4 (1974) 99–106, disclose the synthesis of $CF_3SO_2NAg_2$ made from $CF_3SO_2NAg_2 \cdot NH_3$ at 200° C. $CF_3SO_2NAg_2 \cdot NH_3$ is formed from $CF_3SO_2NH_2$ and $AgNO_3$ in aqueous solution while adding an aqueous solution of ammonia dropwise.

Meußdoerffer et al, Chemiker Zeitung, 96. Jahrgang (1972) No. 10, 582–583 disclose a method for synthesizing $RSO_2NH_2$ where R is perfluoroalkyl.

SUMMARY OF THE INVENTION

The present invention is a composition comprising sulfonyl amide salts, of which at least 50 mol-% of said salts are dimetal sulfonyl amide salts represented by the formula $$(RSO_2NM_b)_{3-b}M'_c \qquad (I)$$

wherein R is aryl, fluoro-aryl, or $XCF_2$— where X is H, halogen, fluorinated or non-fluorinated linear or cyclic alkyl radicals having 1–10 carbon, optionally substituted by one or more ether oxygens, M' is an alkaline earth metal, b=1 or 2, c=0 or 1, M is alkaline earth or alkali metal when b is 1 or 2 respectively and c=0, and M is alkali metal when b=1 and c=1, with the proviso that c≠1 when b=2.

The present invention further provides for a process for forming a dimetal sulfonyl amide salt comprising:

contacting in an atmosphere having a water vapor concentration of less than 50 parts per million,
at least one alkali or alkaline earth hydride,
a sulfonyl amide or monometal sulfonyl amide salt thereof having the formula $$(RSO_2NH)_{3-a}M'' \qquad (II)$$

wherein a=1 or 2, M" is alkaline earth metal when a=1, M" is alkali metal or hydrogen when a=2, and R is aryl, fluoro-aryl, or $XCF_2$— where X is H, halogen, or a fluorinated or non-fluorinated linear or cyclic alkyl radical having 1–10 carbons, optionally substituted by one or more ether oxygens;

and, at least one aprotic liquid substantially free of water, thereby forming a reaction mixture; and,
reacting said reaction mixture forming a precipitate of $(RSO_2NM_b)_{3-b}M'_c$;
and separating said precipitate from said liquid.

As used herein, the term "reacting" is intended to mean allowing at least two components in a reaction mixture to react to form at least one product. "Reacting" may optionally include stirring and/or heating or cooling.

BRIEF DESCRIPTION OF THE DRAWING

FIG. 1 describes the apparatus employed for determining the amount of hydrogen evolved in the process of the invention.

DETAILED DESCRIPTION

The dimetal sulfonyl amide salt $(RSO_2NM_b)_{3-b}M'$, (I), composition of the present invention has surprisingly high efficacy in the preparation of sulfonyl imides including unsaturated and saturated fluorosulfonylimides, and including ionomers having pendant groups comprising fluorosulfonyl imides, which are highly suitable for use in electrochemical cells. In particular, the lithium imide may serve as an electrolyte in lithium and lithium ion batteries. Until the present invention, however, (I), as $CF_3SO_2NNa_2$, the preferred embodiment, was available according to the process of Xue as described in the background, which consists of combining $CF_3SO_2NHNa$ made according to known art with NaH in THF solvent at room temperature, and mixing for four hours. The product of Xue when combined with a cyclic sulfone of the formula

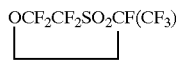 (III)

provides a mixture of fluorosulfonyl imides, by far the most useful of which is the unsaturated compound of the formula

 (IV)

but which is prepared according to Xue in only 4% yield, an amount too small for most or commercial enterprise. The unsaturated monomer (IV) is of considerable potential commercial value for incorporation into ionomers with application in electrochemical end uses. The cyclic sulfone (III) is readily available by reactions taught in the art. There is considerable incentive to find ways to prepare the monomer (IV) from the cyclic sulfone (III).

In the process according to Xue, $CF_3SO_2NHNa$ is combined with NaH in tetrahydrofuran (THF) for four hours at room temperature to form $CF_3SO_2NNa_2$. The inventor hereof has followed the teachings of Xue, and determined by ordinary analytical methods that Xue's process produces $CF_3SO_2NNa_2$ with conversion of less than 10% most of the remainder of the reaction product being unconverted starting material.

The inventor hereof has found surprisingly that the dimetal sulfonyl amide salt (I) can be made at much higher purities than in Xue's process, purity of greater than 50%, preferably greater than 90%, most preferably greater than 95%, by contacting the sulfonyl amide or a monometal salt thereof (II), with at least one alkali or alkaline earth metal hydride and an aprotic liquid to form a reaction mixture which is permitted to react to any desired degree of conversion from 50% up to 100%, which is preferred. In the sulfonyl amide or monometal salt thereof (II), a=1 or 2, M" is alkaline earth metal when a=1, M" is alkali metal or hydrogen when a=2, and R is aryl, fluoro-aryl, or $XCF_2$— where X is H, halogen, or a fluorinated or non-fluorinated linear or cyclic alkyl radical having 1–10 carbons, optionally substituted by one or more ether oxygens. The hydride may be a mixture of more than one alkali or alkaline earth hydrides, or a mixture of alkali and alkaline earth hydrides. If preferred, the reaction may proceed in stages with different hydrides being fed to the reaction vessel at different times.

R is preferably perfluoroalkyl, most preferably trifluoromethyl, and the hydride is preferably sodium hydride. $CF_3SO_2NH_2$ is the preferred starting material. The preferred aprotic liquid is acetonitrile. Preferably, the reaction to produce the $CF_3SO_2NNa_2$ is continued until one or the other starting material is completely consumed and the reaction stops. More preferably the stoichiometry is adjusted so that only trace amounts of either starting material remain when reaction is complete. The hydride is preferably added at slightly below stoichiometric quantity.

Sulfonyl amide and monometal salt thereof (II), are soluble in the aprotic solvents employed in the process of preparing the dimetal sulfonyl amide salt (I), but the dimetal sulfonyl amide salt (I) itself is not. The solubility difference is exploited to separate the reaction product from the reaction mixture and obtain a composition comprising sulfonyl amide salts at least 50 mol %, preferably at least 90 mol %, most preferably at least 95 mol %, of which salts are dimetal sulfonyl amide salts represented by the formula $(RSO_2NM_b)_{3-b}M'$, (I), as hereinabove defined. Any convenient method known in the art for separating solids from liquids may be employed, including filtration, centrifugation and, distillation.

While it is preferred to permit the reaction to run to completion, this may not always be practical depending upon the aprotic solvent chosen. In neat acetonitrile, 100% conversion is achieved in about 4 hours at room temperature. However, in neat THF, six days of reaction is required for 100% conversion. In the latter case, it may be desired to separate the reaction product before the reactants have fully reacted. The method of separation based upon the solubility difference hereinabove described provides a practical method for isolating the dimetal sulfonyl amide salt (I) at high purity when conversion has been low.

It has been found that residual hydride left over from the synthesis of the dimetal sulfonyl amide salt (I) of the present invention is not highly deleterious to the use of (I) in preparing imides from sulfonyl fluorides or cyclic sulfones. While not critical, the $CF_3SO_2NNa_2$ preferred for the process of the present invention is substantially free of contamination by NaH. This is achieved by employing slightly less than the stoichiometric amount of NaH in its preparation thereby insuring that when the reaction achieves full conversion, the NaH will be exhausted. Any excess of the soluble reaction intermediate, $CF_3SO_2NHN_a$, is easily separated by washing/filtration cycles, preferably using fresh aliquouts of solvent.

In preparing the dimetal sulfonyl amide salt (I) it has been found that the components of the reaction mixture may be combined in any order, but that it is preferred to first mix the sulfonyl amide or a monometal salt thereof (II), with the aprotic liquid to form a solution, followed by adding in the hydride to form a slurry after the solution has formed. Mixing the hydride with the aprotic solvent as a first step has resulted in poor reaction or slower than expected conversion.

A suitable temperature for preparing the dimetal sulfonyl amide salt (I) will lie between the melting point and the boiling point of the aprotic liquid selected. It has been found to be satisfactory for the practice of the invention to conduct the process of the invention at room temperature. However, somewhat higher temperatures results in faster reaction. In the most preferred embodiment of the invention, acetontrile is employed as a solvent at a temperature between 0° C. and 80° C., preferably between room temperature and 80° C., most preferably between room temperature and 60° C.

Aprotic solvents suitable for preparing the dimetal sulfonyl amide salt (I) should be substantially free of water. Excess water causes the reaction to reverse, for example to form $CF_3SO_2NHNa$ and NaOH, and provides a route for making a sulfonate instead of an imide. In a preferred embodiment, it has been found satisfactory to employ acetonitrile having water content less than or equal to 500 PPM, with water content less than or equal to 50 PPM more preferred. Acetonitrile is quite hygroscopic, and care should be taken in handling to avoid water contamination from the atmosphere.

The atmosphere to which the dimetal sulfonyl amide salt (I) is exposed should also be substantially free of water. Water vapor concentration of 25 ppm have been found to be highly suitable. Higher levels of water vapor concentration can be tolerated, but it should be understood that the higher the water vapor concentration of the atmosphere, the greater the contamination during subsequent reaction. As a general rule, the less water the better, in whatever form.

The term "inert atmosphere", as used herein, refers to an anhydrous atmosphere having a water vapor concentration of less than about 50 ppm. It is not meant to imply a non-oxidative atmosphere. Thus, the reactions herein may be accomplished in desiccated air as well as in dry nitrogen or other non-chemically active gases. Dry nitrogen gas, however, is preferred.

In a preferred embodiment, $CF_3SO_2NH_2$ is dissolved at a concentration in the range of 5–10% by weight in acetonitrile in an inert atmosphere such as dry nitrogen. At higher concentrations good mixing may become more difficult to maintain as the insoluble $CF_3SO_2NNa_2$ product begins to form, which may create a dispersion. Therefore, at concentrations higher than about 10% by weight, other forms of agitation may be preferred over simple stirring, such as ultrasonic agitation, or microfluidization such as may be achieved using a MicroFluidizer™ available from Microfluidics, Inc., Newton, Mass.

While the inert atmosphere is maintained, NaH is added with agitation continued until the reaction is complete in about four hours. Hydrogen gas evolution rate, determined by any convenient method known in the art, has been found to be an effective indicator of reaction. The cessation of hydrogen gas flow signals completion of the reaction. An apparatus suitable for determining hydrogen gas evolution rate is shown in FIG. 1, and described hereinbelow.

The amount of NaH added depends upon the particular requirements and intentions of the practitioner hereof. Adding a slight excess over the stoichiometric amount of NaH ensures complete conversion of the $CF_3SO_2NH_2$ or in the alternative $CF_3SO_2NHNa$ to $CF_3SO_2NNa_2$. However, this leaves the $CF_3SO_2NNa_2$ so prepared still contaminated with insoluble NaH from which it is difficult to separate although the residual NaH does not appear to cause problems in the intended uses for the $CF_3SO_2NNa_2$ of the present invention. On the other hand, if the goal is to achieve the cleanest possible $CF_3SO_2NNa_2$ then a slight deficit of NaH, below the stoichiometric amount, may be employed to ensure that the NaH will be fully consumed. Employing a deficit of NaH will result in less than complete conversion of the $CF_3SO_2NH_2$ or $CF_3SO_2NHNa$ to $CF_3SO_2NNa_2$. The soluble residual $CF_3SO_2NH_2$ or $CF_3SO_2NHNa$ is easily washed away from the insoluble $CF_3SO_2NNa_2$.

The dimetal sulfonyl amide salt (I) may be dried under vacuum at elevated temperature. A suitable temperature depends upon the specific composition thereof. The preferred $CF_3SO_2NNa_2$ should be dried at a temperature preferably no higher than 80° C., most preferably no higher than 65° C. Certain of the compositions of the invention, including the preferred $CF_3SO_2NNa_2$, have been observed to undergo decomposition aggressively when heated to the decomposition threshold. The compound is moisture sensitive and should be handled under anhydrous conditions. There is a strong possibility of spontaneous and violent decomposition of this material. Spontaneous decomposition at room temperature has been observed. It is highly recommended to never handle this material in a dry state.

The process of the invention is believed to proceed according to the following scheme: one mole of the starting sulfonyl amide (II) is combined with two moles of hydride for complete conversion to one mole of the dimetal sulfonyl amide salt. The reaction proceeds in a first step to effect conversion of the amide (II) first to the monometal salt thereof (II) followed by additional reaction to form the dimetal sulfonyl amide salt (I). Thus the monometal salt (II) is an intermediate formed when the amide (II) is employed as starting material.

The monometal salt (II) can also be made in a separate process according to the known methods of art, and then employed as starting material in the process of the invention.

While residual hydride is not thought to be deleterious to the efficacy of the dimetal sulfonyl amide salt, (I) product in its intended uses, residual monometal amide/salt is not inert and interferes considerably; an exception is the case wherein R is a phenyl group. In certain cases of imidizing sulfonyl fluoride containing compounds having highly sensitive unsaturation, it is found that $PhSO_2NHNa$ acts in a manner similar to that of the $PhSO_2NNa_2$ of the invention in that it does not attack the double bond.

In a preferred embodiment, the aprotic solvent of the process of the invention comprises acetonitrile. Acetonitrile has been found to accelerate the conversion by a considerable amount over other aprotic solvents. In heat acetonitrile, essentially quantitative conversion is achieved in about 4 hours. In the presence of as little as 5% acetonitrile in THF essentially quantitative conversion is achieved in about 25 h. These results contrast starkly with the six days required under the conditions taught by Xue.

It is found in the practice of the invention that solvent selection effects the rate of conversion, though most aprotic solvents will lead to high conversion over sufficient time. Acetonitrile is highly preferred. Other aliphatic and aromatic nitriles, while suitable, do not appear to be particularly better than the THF employed by Xue but may be employed as substitutes for THF. Suitable nitriles include higher alkyl nitriles, dinitriles such as adiponitrile, benzonitrile, and the like. Other suitable solvents include ethers, dimethyl formamide (DMF), dimethylsulfoxide (DMSO), dimethul acetamide (DMAC), and amides. Combinations of suitable solvents are also suitable for the practice of the invention.

Any of the methods hereinabove, alone or in combination, provide a highly purified form of the composition of the invention.

A highly purified form of the dimetal sulfonyl amide salt $(RSO_2NM_b)_{3-b}M'$, (I), greater than 95% purity, is readily achieved in the process of the invention. This purified form is then suitable to perform the various imidization reactions hereinbelow exemplified producing pure product at high yields. The purity of the imidized product depends directly upon the purity of (1) prepared according to the invention. Any of the methods of preparation herein described are capable of providing (I) in purities of greater than 95%.

In the process of the present invention an alkali or alkaline earth hydride is contacted with an aprotic solvent and a sulfonyl amide or monometal salt thereof $(RSO_2NH)_{3-n}M''$ thereby forming a reaction mixture wherein a=1 or 2, M'' is alkaline earth metal when a=1, M'' is alkali metal or hydrogen when a=2, and R is aryl, fluoro-aryl, or $XCF_2$— where X is H, halogen, or a fluorinated or non-fluorinated linear or cyclic alkyl radical having 1–10 carbons, optionally substituted by one or more ether oxygens. Preferably the hydride is sodium hydride, M'' is hydrogen, and R is perfluoroalkyl having 1–4 carbons. Most preferably, R is $CF_3$—. In this process, the larger R is, the slower the reaction and the lower the conversion rate.

The composition of the invention may include a mixture of metals forming the amide salt, including a mixture of alkali and alkaline earth metals in the same molecule. Thus, for example, if two moles of $CF_3SO_2NH_2$ is combined with one mole of $CaH_2$ followed by two moles of NaH, the resulting product will comprise $(CF_3SO_2NNa)_2Ca$. Many other mixtures of metals may be obtained in the current process and are encompassed therewithin.

In one embodiment of the practice of the invention, the reaction mixture is agitated, at a temperature between the freezing point and boiling point of the solvent. Room temperature has been found to be satisfactory in the preferred embodiment. The mixture is permitted to react for as long as is required to reach a degree of conversion of at least 50%. Degree of conversion is conveniently determined by measuring the volume of hydrogen gas evolved according to any method known in the art. Preferably, the reaction is allowed to proceed until no further evolution of hydrogen gas is observed indicating complete reaction. In an embodiment in which excess NaH is employed, this point is found to correspond to the point where no flourine signal can be detected by NMR in the solvent.

Preferably, the dimetal sulfonyl amide salt reaction product (I) is separated from the solvent and any residual starting material, normally by a combination of washing and filtration. It has been found in the practice of the invention that $CF_3SO_2NNa_2$ exhibits slight solubility in either solvents such as THF but is quite insoluble in the preferred solvent, acetonitrile. To facilitate separation, acetonitrile is therefore further preferred.

The composition of the invention, particularly the preferred composition having a molar concentration of $CF_3SO_2NNa_2$ exceeding 90% with respect to the total concentration of sulfonyl amide salt, is surprisingly well-suited to forming imides from sulfonyl fluoride containing fluorinated compounds, as well as for producing a highly desirable fluoromonomer from a fluorocyclic sulfone. The $CF_3SO_2NNa_2$ composition can convert a wide variety of unsaturated compounds having sulfonyl fluoride functionality to the corresponding sodium imide without the need to protect the double bond. Thus, a polymerizable ionic monomer can be prepared therefrom in a single-step reaction. The ionic monomers are of particular utility in forming copolymers with vinylidene fluoride, followed by ion exchange to the lithium imide form, to form a solid polymer electrolyte particularly well-suited for use in lithium and lithium ion batteries.

In like manner, the preferred $CF_3SO_2NNa_2$ composition is also useful in converting polymers having a pendant sulfonyl fluoride functionality to the corresponding sodium imides. In a particularly surprising aspect, polymers comprising partially fluorinated monomer units, most particularly, having vinylidene fluoride monomer units in combination with fluorovinylether sulfonyl fluoride monomer units, can be converted to the corresponding imide without attack on the highly reactive backbone. This represents the only method for performing this reaction. No known method of imidization of sulfonyl fluorides can be performed on polymers having vinylidene fluoride monomer units without attacking the backbone of the polymer.

The process of the present invention as herein described is highly effective at producing the $(RSO_2NM_a)_{3-a}M'$ product at high conversions and high purities at conversion rates which are suitable for commercial purposes. The invention is further illustrated in the following specific embodiments.

EXAMPLES

Example 1

$CF_3SO_2NH_2$ was purchased from Tokyo Chemical Industry, Portland, Oreg., (TCI) and dried and purified by two cycles of sublimation under a vacuum of about 0.1 Pa ($10^{-3}$ Torr), employing a water cooled (−20° C.) cold-finger, and an oil bath at 80° C. Anhydrous acetonitrile was purchased from EM Science Gibbstown, N.J., slurried with $P_2O_5$ and distilled to ensure dryness, and stored over molecular sieves inside a dry box until ready to be used. Sodium hydride (95%) was purchased from Aldrich Chemical.

Inside a model HE-63-P dry-box (Vacuum Atmosphere Company, Hawthorne, Calif.) having a dry nitrogen atmosphere, a round bottom flask was charged with 30,003 g of the sublimed $CF_3SO_2NH_2$ and 750 ml of the dried acetonitrile. 9.003 g of the solution hydride was slowly added over a period of 60 min while the reaction mixture was stirred with a magnetic stir bar. The temperature of the reaction mixture increased from 21.6° C. to 50.5° C. during the addition process. The mixture was stirred at room temperature for 20 h. After 4–5 hours the reaction medium had taken on an opaque "creamy" appearance, and no further bubbling, indicative of the evolution of hydrogen, was observed.

The reaction mixture was filtered through a glass-filter (medium porosity) inside the dry-box. The white solid was washed three times with 100 ml of the anhydrous acetonitrile, transferred from the filter to a Schlenk flask and dried under vacuum of 1 Pa ($10^{-2}$ Torr) at room temperature for 5 h, still in the dry box. Approximately 10% of the filtrate was lost in transferring from the filter to the Schlenk flask. The Schlenk flask was sealed, removed from the dry-box, and subject to further evacuation under oil pump vacuum 0.1 Pa ($10^{-1}$ Torr) for 15 h at room temperature. The Schlenk flask was then immersed in an oil bath set at 50° C. and held for four hours at which time the bath was heated to 65° C. and the Schlenk flask was held therein for an additional 20 h while still subject to evacuation under oil pump vacuum 0.1 Pa ($10^{-3}$ Torr). Afterwards, the $CF_3SO_2NNa_2$ was only handled inside the dry-box.

30.0 grams of product was isolated. The product decomposed at 110° C. while generating large amounts of a gas.

Example 2

Inside the dry box of Example 1, a flask was charged with 5.142 g $C_4F_9SO_2NH_2$ made from $C_4F_9SO_2F$ and $NH_3$ according to the method of Meuβdoerffer et al, op.cit., and 100 ml of anhydrous acetonitrile prepared as in Example 1. 0.784 g NaH (Aldrich) was slowly added over a period of 5 min. The mixture was stirred at room temperature for 24 h without observation. Insoluble $C_4F_9SO_2NNa_2$ had precipitated at the bottom of the flask. The reaction mixture was filtered through a glass filter (fine porosity) and the white residue was washed three times with 50 ml of anhydrous acetonitrile. The residue was collected from the filter and placed in a Schlenk-flask. Afterwards, the material was brought outside the dry-box and dried under oil pump vacuum 0.1 Pa ($10^{-3}$ Torr) for 24 h at an oil bath temperature of 65° C. $C_4F_9SO_2NNa_2$ was only handled inside the dry-box. 4.37 g of product were isolated.

Example 3

Employing the reagents and equipment of Example 1, inside the dry-box 3.123 g of the sublimed $CF_3SO_2NH_2$ was dissolved in 100 ml of the anhydrous acetonitrile in a round-bottom flask. 1.127 g of the sodium hydride was slowly added to form a first reaction mixture. Addition of NaH took place over a period of 10 min while the first reaction mixture was stirred with a magnetic stirring bar at room temperature. After 3 h, no fluorine could be detected by $^{19}F$ NMR in the solution indicating complete conversion of $CF_3SO_2NH_2$ to $CF_3SO_2NNa_2$, thereby forming a mixture of $CF_3SO_2NNa_2$ and acetonitrile, with some residual NaH.

$CF_2$=$CFOCF_2CF(CF_3)OCF_2CF_2SO_2F$ (PSEPVE) prepared according to the method of Connolly et al., U.S. Pat. No. 3,282,875, was slurried with $P_2O_5$ and distilled. 10.002 g of the thus- treated PSEPVE was added to the mixture of $CF_3SO_2NNa_2$ and acetonitrile prepared as hereinabove to form a second reaction mixture. The second reaction mixture was stirred at room temperature. After 10 min, the mixture turned clear, indicative of complete reaction of the $CF_3SO_2NNa_2$, and then slightly cloudy, indicative of the precipitation of the NaF by-product. After 30 minutes fluorine NMR confirmed a substantial concentration of the imidized form of PSEPVE. The reacted mixture was centrifuged and then filtered through a glass filter (medium porosity). The residue was washed with 100 ml of anhydrous acetonitrile. All volatiles were removed under vacuum of 0.1 Pa ($10^{-3}$ Torr) at room temperature and the slightly beige residue was heated to 110° C. for 16 h at 0.1 Pa ($10^{-3}$ Torr). Yield was 9.494 g.

$^{19}$F NMR in $CD_3CN$ confirmed the structure $CF_2=CFOCF_2CF(CF_3)OCF_2CF_2SO_2N(Na)SO_2CF_3$. $^{19}$F NMR in $CD_3CN$/Freon-11 ($CF_2{}^{A,A'}=CF^BOCF_2{}^CCF^D(CF_3{}^E)OCF_2{}^FCF_2{}^GSO_2N(Na)SO_2CF_3{}^H$): −112.6, −120.9 ppm (A, 1F, A', 1F), −135.7 ppm (B, 1F), −78.0 ppm ($CF_2$, C, 2F), −144.2 ppm (CF, D, 1F), −79.1 ppm ($CF_3$, E, 3F), −83.7 ppm ($CF_2$, F, 2F), −116.0 ppm ($CF_2$, G, 2F), −78.9 ppm ($CF_3$, H, 3F). MS: Negative electron spray; 574.14, M—Na.

Example 4

Inside the dry-box of Example 1, a round bottom flask was charged with 5.027 g of the $C_4F_9SO_2NH_2$ made from $C_4F_9SO_2F$ and $NH_3$ according to the method of Meußdoerffer et al, op.cit., and 100 ml of anhydrous acetonitrile prepared as in Example 1. 0.890 g of sodium hydride (Aldrich) was slowly added to form a first reaction mixture. Addition of NaH took place over a period of 10 min while the reaction mixture was stirred at room temperature with a magnetic stir bar. After 22 h of stirring, no fluorine could be detected by $^{19}$F NMR in the solution indicating complete conversion, thereby forming a mixture of $C_4F_9SO_2NNa_2$ in acetonitrile, contaminated by some residual NaH.

7.797 g of the PSEPVE of Example 3 was added to the mixture of $C_4F_9SO_2NNa_2$ and acetonitrile prepared hereinabove to form a second reaction mixture. The second reaction mixture was stirred at room temperature. After 10 min, the mixture turned clear, indicative of complete reaction of the $CF_3SO_2NNa$, and then slightly cloudy, indicating the precipitation of the NaF by-product. NMR of the reaction mixture taken after 30 min confirmed the substantial presence of the imidized form of PSEPVE. The reaction mixture was centrifuged and then filtered through a glass filter (medium porosity). The residue was washed with 100 ml of anhydrous acetonitrile. All volatiles were removed under vacuum and the slightly beige residue was heated to 110° C. for 16 h at 0.1 Pa ($10^{-3}$ Torr). Yield was 8.358 g.

$^{19}$F NMR in $CD_3CN$ confirmed the structure $CF_2=CFOCF_2CF(CF_3)OCF_2CF_2CF_2SO_2N(Na)SO_2(CF_2)_3CF_3$. $^{19}$F NMR in $CD_3CN$/Freon-11 ($CF_2{}^{A,A'}=CF^BOCF_2{}^CCF^D(CF_3{}^E)OCF_2{}^FCF_2{}^GSO_2N(Na)SO_2CF_2{}^HCF_2{}^ICF_2{}^JCF_3{}^K$): −112.6, −120.7 ppm (A, 1F, A', 1F), −135.6 ppm (B, 1F), −78.0 ppm ($CF_2$, C, 2F), −144.1 ppm (CF, D, 1F), −79.1 ppm ($CF_3$, E, 3F), −83.7 ppm ($CF_2$, F, 2F), −115.9 ppm ($CF_2$, G, 2F), −112.6 ppm ($CF_2$, H, 2F), −120.6 ppm ($CF_2$, I, 2F), −125.8 ppm ($CF_2$J, 2F), −79.1 ppm ($CF_3$, K, 3F). MS: Negative electron spray; 723.98, M—Na.

Example 5

Inside the dry-box, a round bottom flask was charged with 3.051 g, of the $CF_3SO_2NH_2$ made in the manner of Example 1 and 100 ml of anhydrous acetonitrile prepared as in Example 1. 1.068 g of the NaH (Aldrich) was added slowly over a period of 5 min. The mixture was stirred at room temperature for 26 h inside the dry-box and checked periodically by fluorine NMR until no fluorine could be detected. 3.27 g $C_6H_5SO_2F$ used as received from Aldrich was added to the flask. The reaction mixture thus formed was stirred at room temperature for 144 h. The reaction mixture was centrifuged and all volatiles were removed from the reaction solution. The residue was dried at 110° C. for 24 h at 0.1 Pa ($10^-$Torr). The residue was redissolved in 100 ml of anhydrous acetonitrile and filtered through a paper filter. All volatiles were removed from the solution. The residue was dried at 110° C. for 16 h at 0.1 Pa ($10^{-3}$ Torr). NMR in $CD_3CN$ and mass spec. confirmed the structure $PhSO_2N(Na)SO_2CF_3$. Yield was 4.284 g. $^{19}$F NMR in $CD_3CN$: −79.9 ppm ($CF_3$, 3F). $^1$H NMR in $CD_3CN$: 7.90 ppm (2H), 7.54 ppm (3H). MS: negative electron spray; 288,09, M—Na.

Example 6

As in Example 1, a round bottom flask was charged with 3.082 g of the $CF_3SO_2NH_2$ prepared as in Example 1 and 100 ml of anhydrous acetonitrile prepared as in Example 1. 1.134 g of the NaH (Aldrich) was added slowly over a period of 5 min. The mixture was stirred at room temperature for 16 h inside the dry-box. No fluorine could be detected by NMR. 2.025 g of $CH_3SO_2F$ (Aldrich, as received) was added. The reaction mixture thus formed was stirred at room temperature for 2 h. The reaction mixture was centrifuged and all volatiles were removed. The residue was dried at 110° C. for 24 h at $10^{-3}$ Torr. The residue was redissolved in 100 ml of anhydrous acetonitrile and filtered through a paper filter. All volatiles were removed from the solution. The residue was dried at 110° C. for 16 h at $10^{-3}$ Torr. Yield was 4.20 g.

NMR in $CD_3CN$ and mass spec. confirmed the structure $CH_3SO_2N(Na)SO_2CF_3$. $^{19}$F NMR in $CD_3CN$: −79.7 ppm ($CF_3$, 3F). $^1$H NMR in $CD_3CN$: 2.966 ppm (3H). MS: negative electron spray; 226.06, M-Na.

Example 7

THF received from Aldrich was refluxed and distilled from sodium metal to provide anhydrous THF. As in Example 1, 0.646 g of the $CF_3SO_2NNa_2$ prepared in Example 1 was suspended in a 50 ml of the thus prepared anhydrous THF. The cyclic sulfone

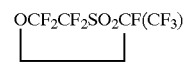

was purchased from the Shanghai Institute of Organic chemistry. The material as received underwent multiple spinning band distillations, and was condensed from $P_2O_5$. 0.900 g of the thus treated cyclic sulfone was added at room temperature while stirring the suspension with a magnetic stir bar. The reaction mixture turned clear indicating complete reaction of the $CF_3SO_2NNa_2$ and a fine powder started to precipitate indicative of the NaF by-product. After 30 min., $^{19}$F NMR in $d^8$-THF confirmed the structure $CF_2=CFOCF_2CF_2SO_2N(Na)SO_2CF_3$.

The reaction mixture was centrifuged for 20 min and then decanted through a glass filter with medium porosity. All volatiles were removed under vacuum and the slightly yellow residue was dried at 100° C. at 0.1 Pa ($10^{-3}$ Torr) oil pump vacuum for 24 h. Yield was 1.057 g. $^{19}$F NMR $d^8$-THF ($CF_2{}^{A,A'}=CF^BOCF_2{}^CCF_2{}^DSO_2N(Na)SO_2CF_3{}^E$); −82.6 ppm (E, 3F), −86.0 ppm (C, 2F), −118.2 ppm, −125.5 ppm (A, 1F, A', 1F), −119.7 ppm (D, 2F), −138.0 ppm (B, 1F).

Example 8

Inside the dry-box of Example 1, 1.200 g of the $C_4F_9SO_2NNa_2$ of Example 2 was suspended in 50 ml of the THF of Example 7.0981 g of the cyclic sulfone of Example 7 was added at room temperature while stirring the suspension with a magnetic stirring bar. The reaction mixture turned clear during the next few hours and a fine powder started to precipitate. $^{19}$F NMR in $d^8$—THF taken after 120 min showed the formation of $CF_2=CFOCF_2CF_2SO_2N(Na)SO_2CF_2CF_2CF_2CF_3$.

The reaction mixture was centrifuged for 20 min and then decanted through a glass filter with medium porosity. All volatiles were removed under vacuum and the slightly yellow residue was dried at 100° C. at 0.1 Pa ($10^{-3}$ Torr) oil pump vacuum for 24 h. The yield was 1.685 g of $CF_2$=CFOCF$_2$CF$_2$SO$_2$N(Na)SO$_2$CF$_2$CF$_2$CF$_2$CF$_3$. $^{19}$F NMR in CD$_3$CN (CF$_2^{A A'}$=CF$^B$OCF$_2^C$CF$_2^D$SO$_2$N(Na)SO$_2$CF$_2^E$CF$_2^F$CF$_2^G$CF$_3^H$): −80.4 ppm (H, 3F), −82.4 ppm (C, 2F), −112.7 ppm (E, 2F), −113.6 ppm, −121.6 ppm (A, 1F, A', 1F), −115.9 ppm (D, 2F), −120.4 ppm (F, 2F), −125.2 ppm (G, 2F), −134.7 ppm (B, 1F).

Example 9

Benzonitrile (Aldrich) was dried by mixing with $P_2O_5$ and then distilling. Employing reagents and equipment of Example 1, inside the dry-box 3.008 g of the sublimed CF$_3$SO$_2$NH$_2$ was dissolved in 90 ml of the dried benzonitrile in a round-bottom flask. To form a first reaction mixture, 1.018 g of the sodium hydride was slowly added while the reaction mixture was stirred with a magnetic stirring bar at room temperature. The reaction mixture changed its appearance after 10 min. A white precipitation was formed causing a thickening of the slurry. Shortly after, the reaction mixture changed its color to yellow. After 60 min, the reaction mixture was red. After 6 h, fluorine could still be detected by $^{19}$F NMR in the solution. After a total of 24 h at room temperature, 8.511 g of PSEPVE of Example 3 was added, thereby forming a second reactions mixture. The second reaction mixture was stirred at room temperature. The color changed from red to yellow. $^{19}$F NMR in CD$_3$CN after 2 h confirmed the formation of the structure CF$_2$=CFOCF$_2$CF(CF$_3$)OCF$_2$CF$_2$SO$_2$N(Na)SO$_2$CF$_3$.

Example 10

In this Example, an apparatus was employed for determining the volume of hydrogen gas evolved by the reaction as a function of time. The apparatus is depicted in FIG. 1. One neck of a three necked round bottom flask, 1, holding a magnetic stirring bar, 2, was fitted with a solid reactant addition device SRAD, 3, having a 75° angle to be employed for feeding a solid to the flask. A second neck was fitted with a thermocouple probe, 4, and a third neck was fitted with a stopcock, 5. The stopcock, 5, was connected via a 4 cm piece of Tygon® tubing, 6, to an Aldrich Safe-purge (TM) valve, 7, containing mineral oil. The Safe-purge valve, 7, was connected via a rubber hose, 8, to a water-filled 250 ml graduated cylinder, 9, that is deployed upside-down in a water-filled 600 ml beaker, 10. The flask, 1, was positioned on a magnetic stirrer, 11. In operation liquid reactants were charged to the flask through any of the necks; SRAD, 3, was charged with the desired amount of solid reactant and reaffixed to the flask, 1, in the downward-pointing position shown in the figure. The beaker, 10, was filled to about 50% of capacity with water while the graduated cylinder, 9, was filled completely with water. The stopcock, 5, was opened, and the adaptor, 3, was inverted thus delivering the solid reactant to the reactants in the flask and thereby initiating the reaction. As hydrogen was evolved from the reaction it displaces the water from the graduated cylinder providing a volumetric means of determining the rate and total amount of hydrogen evolution.

Employing the methods and material of Example 1, inside the dry-box, 0.546 g of the sublimed CF$_3$SO$_2$NH$_2$ was dissolved in 100 ml of the anhydrous acetonitrile in the three neck round bottom flask of FIG. 1. 0.213 g of the sodium hydride was carefully placed in the SRAD. The closed flask was carefully brought outside the dry box and concentrated to the remainder of the apparatus of FIG. 1. After all connections had been established, the stopcock to the reaction flask was opened. The reaction mixture was stirred at room temperature and the SRAD was inverted thereby feeding the NaH to the solution in the flask. Immediately, a reaction could be observed. 80 ml of gas were collected over a period of 5 min. The temperature of the reaction mixture increased from 23° C. to 26° C. Over the next 120 min, the formation of gas slowed down and 74 ml of gas were collected in the graduated cylinder. During this period, the appearance of the reaction mixture changed. The fine residue in the reaction mixture changed to a thicker precipitate that settled easily to the bottom of the flask when the stirring was stopped. The reaction mixture was stirred for another hour at room temperature, 10 ml of additional gas were collected during this period. The flask was brought into the dry box and a sample of the solution was submitted for NMR. No fluorine could be detected, indicating the complete conversion of CF$_3$SO$_2$NHNa into insoluble CF$_3$SO$_2$NNa$_2$.

Example 11

Excess CF$_3$SO$_2$NH$_2$ and NaOH were reacted in water to prepare CF$_3$SO$_2$NNaH. Water and excess CF$_3$SO$_2$NH$_2$ were removed under vacuum of 0.1 Pa ($10^{-3}$ Torr) at 70° C.; the residue was dried for 16 h at 0.1 Pa ($10^{-3}$ Torr) at 110° C. Following the procedures of Example 1, inside the dry box, a 250 m two neck round bottom flask with a magnetic stirring bar was charged with 1.034 g of the CF$_3$SO$_2$NNaH. The material was dissolved in 100 ml of anhydrous acetonitrile of Example 1. The procedures of Example 10 were followed but the three necked flask was replaced by the two-necked flask and the thermocouple was omitted. The reaction mixture was stirred at room temperature and the SRAD was inverted thereby feeding the NaH to the solution in the flask. No immediate reaction could be observed. Over the first 150 min, only a total of 10 ml of an evolving gas. could be collected. After 150 min, the formation of gas started. Over the next 105 min, additional 135 ml of gas were collected in the graduated cylinder. During this period, the appearance of the reaction mixture changed. The fine residue in the reaction mixture changed to a thicker precipitation that settled easily at the bottom of the flask when the stirring was stopped. The reaction mixture was stirred for another 14 h at room temperature. 10 ml of additional gas were collected during this period. The flask was brought into the dry box and a sample of the solution was submitted for NMR. No fluorine could be detected, indicating the complete conversion of CF$_3$SO$_2$NHNa into insoluble CF$_3$SO$_2$NNa$_2$.

Example 12

Following the procedure of Example 11, the flask was charged with 0.939 g of the CF$_3$SO$_2$NHNa which was dissolved in 100 ml anhydrous acetonitrile. 0.214 g of the NaH were placed in the SRAD. After connection to the remainder of the apparatus of FIG. 1, the reaction mixture was stirred at room temperature and the SRAD was inverted thereby feeding the NaH to the solution in the flask. No immediate reaction could be observed. Over the first 3 h, only a total of 5 ml of gas was evolved. Over the next 60 min, the formation of gas was observed and 135 ml of gas were collected in the graduated cylinder. During this period, the appearance of the reaction mixture changed. The fine residue in the reaction mixture changed to a thicker precipitate that settled easily at the bottom of the flask when the stirring was stopped. The gas evolution rate was observed to decrease greatly after about 4 hours of reaction. The reaction mixture was stirred for another 14 h at room temperature. 20 ml of additional gas were collected during this period. The flask was brought into the dry box and a sample of the solution was submitted for NMR. No fluorine could be detected, indicating the complete conversion of CF$_3$SO$_2$NHNa into insoluble CF$_3$SO$_2$NNa$_2$.

Example 13

Following the procedure of Example 11, a 250 ml two neck round bottom flask was charged with 0.189 g NaH and 50 ml of anhydrous acetonitrile prepared as in Example 1. 0.879 g of the $CF_3SO_2NHNa$ prepared in Example 11 was dissolved in 50 ml of anhydrous acetonitrile prepared as in Example 1 and placed in an addition funnel which replaced the SRAD device of Example 11. After making the required connections, the reaction mixture was stirred at room temperature for 4 h. No gas formation was observed. The $CF_3SO_2NHNa$ solution was added and the reaction mixture was continued to be stirred at room temperature. After 18 h, only a total of 20 ml of an evolving gas could be collected. The reaction mixture was bright yellow and did not look like expected. A lot of a yellow precipitate was formed. The reaction mixture was discarded.

The reason why this reaction did not proceed as expected is not known.

Example 14

Following the procedure of Example 10, inside the dry-box, a 250 ml three neck round bottom flask was charged with 75 ml of anhydrous acetonitrile prepared as in Example 1. 0.189 g NaH was placed in the SRAD. 0.879 g of the $CF_3SO_2NHNa$ of Example 10 was dissolved in 25 ml acetonitrile prepared as in Example 1 and placed in an addition funnel which substituted for the thermocouple of Example 10. After the required connections were made, the reaction mixture was stirred at room temperature and the NaH was immediately added to the solvent. 6 ml of gas was collected over a period of 3 h. The $CF_3SO_2NHNa$ solution was added and the reaction mixture was continued to be stirred at room temperature. 1 h 45 min after the addition of the $CF_3SO_2NHNa$, an additional 4 ml of gas had been collected. The reaction mixture turned slightly yellow. 4 h after the addition of the $CF_3SO_2NHNa$, the reaction seemed to start. 6 h and 40 min after the addition of the monosodium solution, a total of 80 ml of gas since the addition had been collected. The reaction mixture was stirred for another 14 h 30 min. A total of 116 ml gas had been collected. 103 ml are the expected amount. The flask was brought into the dry-box and an NMR sample was collected from the solution. Only a trace of a fluorine signal at −80.6 ppm could be detected, indicating the conversion of $CF_3SO_2NHNa$ into insoluble $CF_3SO_2NNa_2$.

2.120 g of PSEPVE prepared as in Example 3 was added to the now bright yellow solution, containing a yellowish solid. The reaction mixture turned orange and after 15 min stirring at room temperature, the reaction mixture turned clear. A fine precipitate formed. An NMR sample was collected after 1 h showing the formation of the product $CF_2=CFOCF_2CF(CF_3)OCF_2CF_2SO_2N(Na)SO_2CF_3$ and excess PSEPVE.

Comparative Example 1

Inside the dry-box of Example 1, a flask was charged with 0.93 g of $CF_3SO_2NHNa$ from Example 11, 0.135 g NaH (Aldrich) and 20 ml of anhydrous THF (Aldrich; distilled off Na metal). The reaction mixture was stirred for 4 h at room temperature and was then filtered through a glass filter (fine porosity). The filtrate was collected in a flask and brought outside the dry-box. All solvents were removed under vacuum 0.1 Pa ($10^{-3}$ Torr) and the residue was heated to 65° C. for 24 h at 0.1 Pa ($10^{-3}$ Torr). 0.862 g (5.04 mmol) of $CF_3SO_2NHNa$ were recovered, corresponding to 92.6% of the starting material. The dried material was brought into the dry-box and 50 ml of anhydrous acetonitrile were added because it is suspected that $CF_3SO_2NNa_2$ is slightly soluble in THF. The majority of the material was dissolved in the acetonitrile and only a slight trace of a solid could be observed in the solution. It was not attempted to separate this residue. It should be safe to assume that less than 10% of the $CF_3SO_2NHNa$ have been converted to $CF_3SO_2NNa_2$ after 4 h in THF at room temperature.

Example 15

Following the procedures of Example 11, inside the dry-box, the round bottom flask was charged with 0.866 g of the $CF_3SO_2NHNa$ of Example 11. The material was dissolved in 100 ml of anhydrous THF (Aldrich; distilled from Na metal; stored over molecular sieves inside the dry-box). 0.171 g of NaH was placed in the SRAD. After the required connections were made according to Example 10, the reaction mixture was stirred at room temperature and the NaH was added to the solution. No obvious reaction could be observed. A total of 113.3 ml of collected hydrogen would represent complete conversion under normalized conditions. The gas collected as a function of time is shown in Table 1.

TABLE 1

| Elapsed time (after addition of NaH) | Gas Collected (ml) | estimated % conversion |
|---|---|---|
| 0 h 45 min | 4 | 3.5 |
| 2 h 30 min | 10 | 8.8 |
| 5 h 45 min | 10 | 8.8 |
| 21 h 45 min | 18 | 15.9 |
| 26 h 15 min | 25 | 22.1 |
| 32 h 45 min | 28 | 24.7 |
| 47 h | 38 | 33.6 |
| 49 h 15 min | 43 | 38.0 |
| 53 h 30 min | 47 | 41.6 |
| 84 h 45 min | 53 | 46.9 |
| 86 h 45 min | 55 | 48.6 |
| 97 h 15 min | 65 | 57.5 |
| 118 h | 78 | 69.0 |
| 122 h 15 min | 85 | 75.2 |
| 139 h 45 min | 110 | 97.3 |
| 142 h | 114 | 100.5 |

The reaction was complete after six days at room temperature. The reaction flask was brought inside the dry-box.

2.511 g of PSEPVE prepared as in Example 3 was added to the colorless reaction mixture that contained a white solid. After 10 min stirring at room temperature, the reaction mixture turned clear. A fine precipitation formed. An NMR sample was collected after 1 h showing the formation of the product $CF_2=CFOCF_2CF(CF_3)OCF_2CF_2SO_2N(Na)SO_2CF_3$ and excess PSEPVE.

Example 16

Following the procedure of Example 11, inside the dry-box, the round bottom flask was charged with 0.633 g of the $CF_3SO_2NHNa$ of Example 11. The material was dissolved in 100 ml of anhydrous acetontrile prepared as in Example 1. 0.103 g of NaH was placed in the SRAD. After the required connections were made, the reaction mixture was stirred and heated by immersing the flask in an oil-bath set at 50° C. The reaction mixture was heated for 2 h and the pressure was allowed to equalize inside the flask. No pressure was released through the bubbler for 30 min. After 2 h of heating, the NaH was added to the solution. No obvious reaction could be observed for 20 min. After 20 min., gas was released from the reaction mixture. Evolution of ca. 83 ml of gas was calculated to correspond to complete conversion.

TABLE 2

| Elapsed time (after addition of NaH) | Gas Collected (ml) |
|---|---|
| 0 h 20 min | 0 |
| 0 h 25 min | 25 |
| 0 h 30 min | 71 |
| 0 h 35 min | 85 |
| 1 h 0 min | 91 |

The formation of gas stopped after 1 hour. The gas collection record is shown in Table 2. The reaction mixture was stirred for another hour at 50° C. oil bath temperature with no further accumulation of gas. The reaction flask was brought inside the dry-box and an NMR sample was taken from the clear solution above the white residue. Only a trace of a fluorine signal at −80.6 ppm could be detected in the noise of the NMR spectrum, indicating the conversion of $CF_3SO_2NHNa$ into insoluble $CF_3SO_2NNa_2$.

1.740 g of PSEPVE prepared as in Example 3 was added to the colorless reaction mixture that contained a white solid. The reaction mixture turned yellow and after 10 min stirring at room temperature, the reaction mixture turned clear. A fine precipitation formed. An NMR sample was collected after 1 h showing the formation of the product $CF_2=CFOCF_2CF(CF_3)OCF_2CF_2SO_2N(Na)SO_2CF_3$ and excess PSEPVE.

Example 17

Following the procedure of Example 11, the flask was charged with 1.195 g of the $CF_3SO_2NHNa$ which was dissolved in a mixture of 95 ml of THF and 5 ml of anhydrous acetonitrile. 0.195 g of the NaH were placed in the SRAD. After connection to the remainder of the apparatus of Example 10, the NaH was added to the reactants in the flask. No immediate reaction could be observed. Over the first 1 h, only a total of 4 ml of gas was evolved. Over the next 5 h, only a total of 7 ml of the expected 157 ml Hydrogen gas had been collected. The reaction mixture was stirred for a total of 25 h at room temperature without further observation. 160 ml of gas were collected during this period.

4.500 g of PSEPVE prepared as in Example 3 was added to the colorless reaction mixture that contained a while solid. The reaction mixture did not change its color and after 10 min stirring at room temperature, the reaction mixture turned clear. A fine precipitation formed. An NMR sample was collected after 1 h showing the formation of the product $CF_2=CFOCF_2CF(CF_3)OCF_2CF_2SO_2N(Na)SO_2CF_3$ and excess PSEPVE.

Example 18

Employing the reagents and equipment of Example 1, inside the dry-box 3.033 g of the sublimed $CF_3SO_2NH_2$ was placed in a round bottom flask and dissolved in 50 ml of the anhydrous acetonitrile. 1.511 g of $CaH_2$ (Aldrich; 90–95%) was added. The reaction mixture was stirred with a magnetic stir bar at room temperature for 48 h. No fluorine could be detected in the reaction mixture after this time period by NMR, indicating the complete conversion of $CF_3SO_2NH_2$ to $(CF_3SO_2NCa)_2$.

9.461 g of PSEPVE prepared as in Example 3 was added and the reaction mixture was stirred at room temperature. No conversion to the product could be observed after 24 h at room temperature.

The reaction mixture was heated to 60° C. for 7 days. The reaction mixture was filtered inside the dry-box through a glass filter (medium porosity) and the flask with the collected solution was brought outside the dry-box. All volatiles were removed under vacuum 0.1 Pa ($10^{-3}$ Torr) and the beige residue was heated to 100° C. at 0.1 Pa ($10^{-3}$ Torr) for 16 h. $^{19}$F NMR in $CD_3CN$ confirmed the structure $(CF_2=CFOCF_2CF(CF_3)OCF_2CF_2SO_2NSO_2CF_3)_2Ca$. Yield was 1.729 g. $^{19}$F NMR in $CD_3CN$
$(CF_2{}^{A,A'}=CF^{B}OCF_2{}^{C}CF^{D}(CF_3{}^{E}) OCF_2{}^{F}CF_2{}^{G}SO_2NSO_2CF_3{}^{H})_2Ca$: −114.3, −122.7 ppm (A, 1F, A', 1F), −137.3 ppm (B, 1F), −79.5 ppm ($CF_2$, C, 2F), −145.9 ppm (CF, D, 1F), −80.9 ppm ($CF_3$, E, 3F), −85.5 ppm ($CF_2$, F, 2F), −117.6 ($CF_2$, G, 2F), −80.6 ppm ($CF_3$, H, 3F). MS: Negative electron spray; 573.98, (M—Ca)/2.

What is claimed is:

1. A composition comprising sulfonyl amide salts of which said salts are at least 50 mol-% sulfonyl amide salts represented by the formula $(RSO_2NM_b)_{3-b}M'_c$ wherein R is aryl, fluoro-aryl, or $XCF_2$— where X is H, halogen, fluorinated or non-fluorinated linear or cyclic alkyl radicals having 1–10 carbons, whereof one or more said carbons may optionally be replaced by ether oxygen, M' is an alkaline earth metal, b=1, or 2, c=0 or 1, M is alkaline earth or alkali metal when b is 1 or 2 respectively and c=0, and M is alkali metal when b=1, and c=1, with the proviso that c 1 when b=2.

2. The composition of claim 1 wherein at least 90 mol-% of said sulfonyl amide salts are represented by the formula $(RSO_2NM_b)_{3-b}M'_c$.

3. The composition of claim 1 wherein R is perfluoroalkyl.

4. The composition of claim 3 wherein R is trifluoromethyl.

5. The composition of claim 1 wherein M is Na and b=2.

6. A process for forming a sulfonyl amide salt, the process comprising combining in an atmosphere having a water vapor concentration of less than 50 parts per million at least one alkali or alkaline earth hydride, a sulfonyl amide or monometal sulfonyl amide salt thereof having the formula $$(RSO_2NH)_{3-a}M'' \quad (II)$$

wherein a=1 or 2, M'' is alkaline earth metal when a=1, M'' is alkali metal or hydrogen when a=2, and R is aryl, fluoro aryl, fluoro-aryl, of $XCF_2$— where X is H, halogen, or a fluorinated or non-fluorinated linear or cyclic alkyl radical having 1–10 carbons , whereof one or more said carbons may optionally be replaced by ether oxygen;

and an aprotic liquid comprising acetonitrile, wherein the acetonitrile is substantially free of water, thereby forming a reaction mixture; and, reacting said reaction mixture forming a precipitate of $(RSO_2NM_b)_{3-b}M'_c$;

and separating said precipitate from said liquid.

7. The process of claim 6 wherein the hydride is sodium hydride.

8. The process of claim 6 wherein R is perfluoroalkyl.

9. The process of claim 9 wherein R is trifluoromethyl.

10. The process of claim 6 further comprising the step of heating the mixture to a temperature in the range of room temperature to 60° C.

11. The process of claim 6 wherein the conversion is at least 90 mol %.

12. The process of claim 6 wherein M'' is H.

13. The process of claim 6 wherein the aprotic liquid and the $(RSO_2NH)_{3-a}M''$ are mixed to form a solution at the same time as or prior to the addition of the hydride.

* * * * *